United States Patent [19]

Vit

[11] 3,998,945
[45] * Dec. 21, 1976

[54] DENTAL TREATMENT
[75] Inventor: Jeroslav Vit, Belle Mead, N.J.
[73] Assignee: National Patent Development Corporation, New York, N.Y.
[ * ] Notice: The portion of the term of this patent subsequent to Jan. 13, 1993, has been disclaimed.
[22] Filed: June 24, 1975
[21] Appl. No.: 589,683

Related U.S. Application Data

[62] Division of Ser. No. 301,163, Oct. 26, 1972, Pat. No. 3,932,605.

[30] Foreign Application Priority Data

| June 29, 1972 | United Kingdom | 30611/72 |
| June 12, 1972 | United Kingdom | 27443/72 |
| Aug. 24, 1972 | United Kingdom | 39588/72 |
| Aug. 24, 1972 | United Kingdom | 39589/72 |

[52] U.S. Cl. .................................. 424/53; 424/54
[51] Int. Cl.$^2$ ........................................ A61K 7/20
[58] Field of Search .................... 424/54, 53, 319; 252/186–188, 94–99

[56] References Cited
UNITED STATES PATENTS

| 3,749,672 | 7/1973 | Golton et al. | 252/95 |
| 3,843,548 | 10/1974 | James | 25/187 |
| 3,886,266 | 5/1975 | Goldman et al. | 424/53 |
| 3,932,605 | 1/1976 | Vit | 424/51 |

Primary Examiner—Shep K. Rose
Attorney, Agent, or Firm—Cushman, Darby & Cushman

[57] ABSTRACT

N-haloamines also containing a hydroxy group, a sulfonic acid group, and N-acyl group or a carboxylic acid group are useful in treating teeth to remove caries, dissolve or remove plaque, to help in the prevention of calculus formation and in the brightening of teeth. The compounds can be used in solution or in carrier form as a paste.

11 Claims, No Drawings

DENTAL TREATMENT

This is a division of application Ser. No. 301,163 filed Oct. 26, 1972, now U.S. Pat. No. 3,932,605.

The present invention relates to the treatment of teeth in dentistry and to the cleaning of teeth both in dentistry and in personal hygiene.

An object of the invention is to provide a method of treating teeth in dentistry for the removal of plaque and caries, and prevention of the building up of calculus.

Another object is to provide a method of treating teeth in dentistry which removes only plaque and caries, whilst leaving the remainder of the tooth unaffected.

Yet another object is to provide a method of treating teeth in dentistry by removing plaque and caries, thus reducing the needs of mechanical removal by drills, burrs and hand tools to a minimum of eliminating them completely.

A still further object is to provide a method of treating teeth in dentistry which, even if accidentally prolonged beyond an optimum period, will remove only plaque and caries and leave the remainder of the tooth, e.g., dentine or enamel, entirely unaffected.

A still further object is to provide a method of treating teeth in dentistry, for removal of plaque and caries, which is completely painless to the patient, in that it avoids vibration resulting from use of power operated tools, and pressure on sensitive portions of a tooth by hand-manipulated tools.

The brightening of teeth is a persistent goal of modern dentistry. By their nature, teeth are easily stained, and difficult to clean effectively, and it is accordingly necessary for efficient cleaning agents to be used.

Known cleaning agents, whilst being effective to clean teeth, also tend to corrode metal parts of dental appliances and fitments. For example, aqueous sodium hypochlorite has been used hitherto as a tooth brightener, but is not currently used because of its corrosive and therefore destructive effects.

It is therefore an additional object of this invention to provide a tooth brightening agent which is effective in cleaning the teeth but is not corrosive to metal parts.

Another object is to provide an agent for regular use in personal hygiene, say on an everyday basis, for removing stains from the teeth, and/or preventing the build-up of stains, thereby brightening the teeth.

Yet another object is to provide a cleaning agent, for brightening the teeth, which can be manufactured and sold in tablet form for use in water, as a mouth-wash.

A further object is to provide a cleaning agent, for brightening the teeth, which can be produced by mixing of two solutions, at the time of use, for use as a mouth-wash.

It has now been found that the above mentioned objects can be attained by treating teeth to remove caries, dissolve (or otherwise remove plaque), prevent calculus formation and brighten teeth can be accomplished by bringing the teeth into contact with an N-haloamine also containing a hydroxy group, a sulfonic acid group, an N-acyl group or a carboxylic acid group. The halogen has an atomic weight of 35 to 127. Unless otherwise indicated in the present specification and claims the term "N-halo" means "N-monohalo".

The N-halo compounds of the present invention are normally employed in aqueous solution but they can be employed in thicker compositions such as toothpastes.

Many of the N-Halo compounds are unstable and they are conveniently prepared by reacting an alkali metal or alkaline earth metal hypohalite, preferably hypochlorite, with the amino compounds.

Suitable hypohalites are of the formula MOX and/or $M^2X(OX)$ and/or $M^2(OX)_2$, where M is Li, Na, K, Rb, or Cs, and where $M^2$ is Ca, Sr, or Ba, and where X is Cl, Br and/or I.

Examples of suitable hypohalites include sodium hypochlorite, potassium hypobromite, sodium hypoiodite, potassium hypoiodite, potassium hypobromite, rubidium hypochlorite cesium hypochlorite, calcium hypobromite, strontium hypochlorite and barium hypochlorite.

For reacting with the hypohalite to form the N-halo compounds of the invention there can be used either inorganic compounds such as sulfamic acid or organic compounds containing 2 to 11 carbon atoms, e.g. glycine, sarcosine, alpha-aminoisobutyric acid, taurine, 2-aminoethanol, N-acetylglycine, alanine, beta-alanine, serine, phenyl alanine, norvaline, leucine, isoleucine proline, hydroxyproline, omega aminoundecanoic acid, aspartic acid, glutamic acid, asparagine, valine, tyrosine, threonine, cysteine, cystine, methionine, glutamine, tryptophane, histidine, arginine, lysine, alpha-aminobutyric acid, gamma-amino-butyric acid, alpha, epsilon diamino pimelic acid, ornithine, hydroxyl lysine, anthranilic acid, p-aminobenzoic acid, sulfanilic acid, orthanilic acid, phenyl sulfamic acid, aminopropanesulfonic acid 2-aminoethanol, 2-aminopropanol, diethanolamine ethylenediamine tetraacetic acid (EDTA) nitrilotriacetic acid, taurine and aminomethanesulfonic acid; polypeptides, e.g. glycylglycine, glycylglycylglycine etc., also can be used.

Examples of N-halo compound include N-chloroglycine, N-Bromoglycine, N-iodoglycine, N-chlorosarcosine, N-bromosarcosine, N-iodosarcosine, N-chloro alpha amino isobutyric acid, N-chlorotaurine, N-bromotaurine, N-iodotaurine, N-chloroaminomethanesulfonic acid N-chloroethanolamine, N-chloro-N-acetyl glycine, N-bromoethanolamine, N-iodoethanolamine, N-iodo-N-acetyl glycine, N-bromo N-acetyl glycine, N-chloroalanine, N-chloro beta alanine, N-bromo beta alanine, N-chloroserine, N-bromoserine, N-iodoserine, N-chloro-N-phenylalanine, N-chloroisoleucine, N-chloro-norvaline, N-chloroleucine, N-bromoleucine, N-iodoleucine, N-chloroproline, N-bromoproline, N-iodoproline, N-chloro hydroxyproline, N-chloro omega aminoundecanoic acid, N-chloroaspartic acid, N-bromoaspartic acid, N-chloroglutamic acid, N-iodoglutamic acid, N-chlorovaline, N-chlorotyrosine, N-bromo-tyrosine, N-iodotyrosine, N-chloroethreonine, N-chlorocysteine, N-chlorocystine, N-chloromethionine, N-chlorohistidine, N-chloroarginine, N-chloroglutamine, N-bromoglutamine, N-chlorolysine, N-chloro gamma aminobutyric acid, N-chloro alpha, epsilon diaminopimelic acid, N-chloro-ornithine, N-chloro hydroxy lysine, N-chloroanthranilic acid, N-chloro p-aminobenzoic acid, N-chlorosulfanilic acid, N-chloro phenylsulfamic acid, N-chloro aminopropanesulfonic acid, N-chloropropanolamine, N-chloro-diethanolamine, N-chloro ethylene diamine tetraacetic acid (in this compound the nitrogen atom apparently functions as a quaternary nitrogen).

Preferably there are employed N-halo amino carboxylic acids, e.g. aminoalkanoic acids free of divalent sulfur or free of a heterocyclic ring since when the divalent sulfur atom or the heterocyclic ring is present the N-halo compound has a very short half life.

The N-bromo and N-iodo compounds are the most effective but they have shorter half lifes than the N-chloro compounds and hence the N-chloro compounds are usually employed. Preferably the N-halo amino group is directly attached to an aliphatic carbon atom. Compounds which have an unpleasant odor preferably are not employed.

In Goldman et al application Ser. No. 197,966 filed Nov. 11, 1971 there is disclosed the treatment of teeth to remove caries, dissolve plaque and prevent the development or buildup of calculus by the use of sodium, potassium or calcium hypochlorite at a pH of 9 to 11.5. Goldman et al disclose there can be used non toxic buffering agents and states that a preferred buffering agent is a mixture of glycine, sodium chloride and sodium hydroxide and specifically shows a mixture of an 0.5% solution of sodium hypochlorite, 1% glycine hydrochloride and sufficient sodium hydroxide to bring the pH to about 10.0. He also discloses adding a mixture of 1 ml of flavor, 98 ml of a buffer solution 0.05 molar in glycine, 0.05 mole in sodium hydroxide and 0.05 molar in sodium chloride and 1 ml of 5% NaOCl to 500 ml of water and making the product up to 1000 ml with water. While Goldman et al did not realize it they were making N-chloroglycine in situ by this procedure and it was the N-chloro glycine which was the active agent in their process. Applicant makes no claim to what is disclosed in said Goldman et al application (The entire disclosure of which is hereby incorporated by reference) but to make the disclosure complete will set forth examples including N-chloroglycine.

Sodium hypochlorite and the other hypochlorites are irritating to the mucous lining of the mouth. Hence it is desirably not present in the final solution.

The parent nitrogen containing compound is preferably used in excess, e.g., the molar ratio of the parent nitrogen containing compound to available $X^+$ (from the hypochlorite) should be 1:1 or greater, and preferably in the range of 2:1 to 15:1, most preferably 7:1. A mixture of nitrogen containing compounds can be used.

The available active $X^+$ concentration should preferably lie between 0.01% and 6%, and more preferably 0.05% and 1%.

The solutions should be used at a pH in the range of pH 8 to 12 and more preferably in the range of pH 10.5 to 11.5 inclusive, most preferably 11 to 11.5.

To maintain the preferred Ph range it is desirable, because hydrogen ions are generated during the decomposition of an N-halo compound in aqueous solution to add a buffer system to the solution for dental or brightener treatment. Such buffer should be compatible with the N-halo compound, i.e. it should not have any deleterious effect thereon and it should be non-toxic. Borates and phosphates are examples of compatible salts for the formation of buffer systems, e.g., $Na_2B_4O_7$ can be used as the buffer since it can hold the pH above 10 even though in other systems it usually buffers at a lower pH.

Of course mixtures of N-halo compounds can be employed.

The stability of N-halo compounds in water solutions is limited, and is generally increased with a decrease of pH. The stability of an N-halo compound can conveniently be specified in terms of its "half-life", that is to say the time required for decomposition of one-half of the N-halo compound present in solution. An illustrative range of half-life values for solutions for use to remove or dissolve plaque or as tooth brighteners is, for example, within the range of 3 minutes to 60 minutes, and advantageously 10 to 20 minutes; for caries removal longer half lives are desirable. For example, the half-life of N-chloro compounds can be adjusted using a buffer of the type set forth above to maintain the proper pH.

The method of the present invention needs the solution only to be brought adequately into contact with the teeth for a short period to enable the plaque to be removed or to brighten teeth.

The removal may be accelerated by feeding the solution onto the affected tooth as a stream, and an erosive effect may be obtained during the course of the removal of the plaque and carious material. The erosive effect may itself be hastened by providing a pulsating stream which weakens the deposits of plaque and caries by alternate application of force followed by relaxation, resulting in mechanical fatiguing of the deposits. Also, the use of hand tool scraping helps in removing caries.

By addition of a suitable carrier, e.g., a thickening agent, such as $SiO_2$, to form a paste, the solution may be more readily applied with an applicator such as a toothbrush or the like. Such as paste can be applied one or more times a day to the teeth.

Where a solution is employed it is also possible to dissolve one or more solid materials, for example in water or aqueous solution.

The teeth are then brightened or plaque removal by simply taking a portion of the resulting solution into the mouth as a mouth wash.

In any of the materials are provided in tablet form, it is advantageous to add means for causing effervescence to increase the rate of dissolution of the tablet material(s). By way of example, equal amounts of adipic acid and sodium bicarbonate in a tablet cause effervescence upon dissolution.

Tablets in accordance with the invention may also include other materials, e.g., fillers, so long as they are compatible.

Repeated use of these solutions over a prolonged period, say 4 weeks, can be used to bring teeth up to a desired standard of brightness and to prevent build up of plaque. Thereafter, continued daily use of the mouth wash maintains the condition of the teeth.

Unless otherwise indicated all parts and percentages are by weight.

In carrying out the method of the present invention, the following solutions are illustrative of those which have been found effective.

|   | NaOCl | NaOH | NaCl | Amino Compound | Buffer Salt | pH* |
|---|---|---|---|---|---|---|
| A | 0.008 | 0.0539 | 0.050 | 0.05 glycine | $Na_2HPO_4$ 0.0025 | 11.59 |
| B | 0.008 | 0.0640 | 0.050 | 0.05 glycine | $Na_2B_4O_7$ 0.00125 | 10.77 |

-continued

|   | NaOCl | NaOH | NaCl | Amino Compound | Buffer Salt | pH* |
|---|---|---|---|---|---|---|
| C | 0.008 | 0.0210 | 0.050 | 0.05 glycine | $Na_2B_4O_7$ 0.00125 | 9.65 |
| D | 0.008 | 0.0537 | 0.050 | 0.05 sulfamic acid | None None | 11.49 |
| E | 0.008 | 0.0520 | 0.052 | 0.05 sulfamic acid | None None | 10.75 |
| F | 0.008 | 0.0548 | 0.050 | 0.05 taurine | None None | 11.86 |

*The pH value of all solutions tested remained constant within 0.2 pH units for at least one hour.

EXAMPLE I

The following is a first example of preparation of a decayed tooth for filling.

Solutions A through F were applied as a liquid stream at a temperature of 35°–45° C, and preferably at body temperature circa 37° C, on a carious area of a decayed tooth. The solution was applied either at a steady pressure in the range of 10 to 100 psi., or as a pulsating jet stream where the pressure is varied from 0 to 10 psi. or from 0 to 40 psi., or from 0 to 80 psi., or from 0 to 100 psi., during one cycle at a frequency of 100 to 1500 cycles per minute through a hypodermic needle of 20 to 23 gauge. However, the pressure in either case can be increased to 200 psi.

Each tooth was substantially cleaned and ready to fill within 1 to 7 minutes, depending on the size of the cavity and its location. Judged by qualitative eye observation, the removal of caries is more effective on living unextracted teeth than on extracted teeth. A pulsating jet stream was found to be more efficient than a non-pulsating stream, even though more of the cleansing solution was used in the non-pulsating jet stream.

The following is a table showing the results obtained, using the solutions "A" to "F" on extracted teeth.

Caries Removal

| Solution | Temp. (° C) | Needle Gauge | Frequency (c/min) | Pressure (psi) | Volume (ml) | Time for Complete Removal (min) |
|---|---|---|---|---|---|---|
| A | 37 | 20 | 850 | 0–10 | 430 | 3.5 |
| A | 37 | 20 | 650 | 0–40 | 380 | 4.5 |
| A | 36 | 20 | 700 | 0–40 | 500 | 4.5 |
| A | 37 | 20 | 200 | 0–100 | 470 | 6.0 |
| A | 37 | 23 | —* | 40* | 1150 | 11 |
| B | 38 | 20 | 100 | 0–80 | 480 | 4.5 |
| C | 37 | 20 | 1100 | 0–40 | 460 | 5.0 |
| D | 39 | 20 | 750 | 0–40 | 420 | 5.5 |
| A | 38 | 23 | 1500 | 0–100 | 510 | 7.0 |
| A | 45 | 20 | 550 | 0–40 | 570 | 3.5 |
| A | 35 | 20 | 800 | 0–80 | 490 | 1.0 |
| E | 37 | 20 | 650 | 0–40 | 480 | 4.5 |
| F | 38 | 20 | 800 | 0–80 | 590 | 6.0 |

*Constant non-pulsating jet stream.

A major advantage of this method of treatment, as compared to the established drilling procedure, is that even if the treatment is greatly prolonged (i.e., continued long after all the carious material is removed), no removal of or damage to healthy tooth tissue — dentine or enamel — results. This is, however, not the case if mechanical drilling is accidentally prolonged.

EXAMPLE II

The following is a second example of preparation of a decayed tooth for filling.

An active solution was generated by mixing equal volumes of a 0.1% sodium hypochlorite solution with a 0.1 Molar solution of EDTA. The pH of the EDTA solution was adjusted to 10.5 before mixing. The final solution was used at a temperature of 36° C. This solution was applied in the form of a pulsating jet stream of which the pressure varied from 0 – 80 psi. during one cycle at a frequency of 700 cycles per minute through a 20 gauge needle. The tooth was essentially clean and ready to fill within 5 minutes.

EXAMPLE III

The following is an example of carrying out the method of this invention utilizing the solution as a mouth wash.

An active solution was prepared by mixing equal volumes of 0.2% sodium hypochlorite solution and 0.3 Molar EDTA solution at room temperature. A 20 ml. portion was taken and used for rinsing the patient's oral cavity. The solution was used for approximately one minute. The above procedure was repeated one time for a total rinsing time of two minutes.

EXAMPLE I

A solution for use as a mouth wash, plaque removal and tooth brightener was prepared by mixing equal volumes of aqueous hypohalite and aqueous nitrogen containing compound (or compounds) solution. The initial pH value of the nitrogen containing compound solution was adjusted as necessary using sodium hydroxide. A 20 ml portion of the resulting solution was taken and used to rinse the oral cavity as a mouth wash for approximately one minute. Repeated daily use brightened the subject's teeth, and maintained a desirable level of brightness and removed plaque. The quantities of all ingredients and conditions are specified in Table I, in which the hypohalite ($OX^-$) concentration is in percentages and all other concentrations are in Moles/l.

TABLE I

| Hypohalite Solution | | Nitrogen Containing Compound Solution | | |
|---|---|---|---|---|
| | | Components | | Initial pH |
| NaOCl | 0.1 | Glycine | 0.1 | 11.1 |
| | | NaCl | 0.1 | |
| KOBr | 0.1 | Taurine | 0.1 | 11.2 |
| | | KCl | 0.1 | |
| CaCl(OCl) | 0.16 | Urea | 0.1 | 10.9 |
| | | NaCl | 0.1 | |
| NaOCl | 0.1 | Sulfamic Acid | 0.06 | 11.1 |
| | | Glycine | 0.06 | |
| NaOCl | 0.1 | Ethylenediamine-tetraacetic Acid | 0.1 | 11.0 |
| NaOI | 0.1 | Glycine | 0.16 | 11.0 |
| | | NaI | 0.1 | |
| NaOCl | 0.1 | Glycine | 0.1 | 11.2 |
| | | NaCl | 0.1 | |
| | | $Na_2HPO_4$ | 0.01 | |

EXAMPLE 2

The same method as given in Example 1 was followed except that the solution was prepared by the addition of a solid tablet of $Ca(OCl)_2$ (0.005 moles) and a tablet of glycine (0.05 moles) and $NaHCO_3$ (0.05 moles) per 1 liter of final aqueous solution.

EXAMPLE 3

The method of Example 1 was followed, with the addition that each of the solutions were thickened using $SiO_2$ and then equal volumes of the resulting pastes were mixed and applied with a brush.

EXAMPLE 4

The method of Example 1 was used with the exception that the hypohalite was added as a solid (Ca-(OCl)$_2$, 0.004 moles/l.) to a solution of glycine (0.05 M), NaCl (0.05 M) adjusted to a pH of 11.2.

EXAMPLE 5

The method of Example 1 was used, but the solution was formed by adding solid N-chlorosarcosine (0.008 moles/l) to an aqueous solution of sarcosine (0.042 M), NaCl (0.05 M) and NaOH (0.05M).

EXAMPLE 6

The method of Example 1 was used but with the exception that a previously formed solution of a stable N-halo compound was added to a solution with another nitrogen containing compound. All data are to be found in Table II. All quantities are in moles/l of each initial solution.

TABLE II

| Halo Compound | | Nitrogen Containing Compound Solution | | |
|---|---|---|---|---|
| | | Components | | Initial pH |
| N-chlorotaurine | 0.01 | Glycine | 0.1 | 11.3 |
| | | NaCl | 0.1 | |

When the amino compound has an asymmetric carbon atom there can be used either the DL, the D or the L form. Unless otherwise indicated the racemic form was employed.

Illustrative of aqueous compositions containing N-halo compounds formed in situ and useful in the present invention are those set forth in the following example. The half life times are for the N-halo compound and are in minutes except when h indicates hours or d indicates days. All amounts are in moles per liter.

EXAMPLE 6

| Exp. | Nitrogen Compound | Amt. | NaOH Amt. | NaCl Amt. | NaOCl Amt. | 50% Decomposed |
|---|---|---|---|---|---|---|
| 1 | Glycine | 0.05 | 0.05 | 0.05 | 0.0078 | 53.8 |
| 2 | Glycine | 0.0444 | 0.0444 | 0.0615 | 0.0069 | 52.3 |
| 3 | Glycine | 0.1 | 0.1 | 0.115 | 0.156 | 20.0 |
| 4 | Glycine | 0.05 | 0.05 | 0.065 | 0.0078 | 44.2 |
| 5 | Glycine | 0.025 | 0.025 | 0.040 | 0.0039 | 110.2 |
| 6 | Glycine | 0.0125 | 0.0125 | 0.0279 | 0.0020 | 212.0 |
| 7 | Glycine | 0.005 | 0.05 | 0.05 | 0.0078 | 6.3 |
| 8 | Ethanolamine | 0.05 | 0.05 | 0.05 | 0.0078 | 472.0 |
| 9 | Taurine | 0.05 | 0.05 | 0.05 | 0.0078 | 128.4 h |
| 10 | N-acetyl glycine | 0.05 | 0.05 | 0.05 | 0.0078 | 885.0 |
| 11 | Sarcosine | 0.05 | 0.05 | 0.05 | 0.0078 | 108.0 |
| 12 | Sulfamic acid | 0.05 | 0.05 | 0.05 | 0.0078 | 21 d (for 25% decomposition) |
| 13 | L(+)Glutamic acid | 0.05 | 0.05 | 0.05 | 0.0081 | 25.3 |
| 14 | L(+)Glutamic acid | 0.05 | 0.10 | 0.05 | 0.0081 | 42.8 |
| 15 | DL - Aspartic acid | 0.05 | 0.10 | 0.05 | 0.0081 | 32.8 |
| 16 | L+ Lysine | 0.05 | 0.05 | 0.05 | 0.0081 | 107.0 |
| 17 | L - Leucine | 0.05 | 0.05 | 0.05 | 0.0081 | 58.9 |
| 18 | EDTA | 0.05 | 0.10 | 0.05 | 0.0080 | 13.0 |
| 19 | DL Threonine | 0.05 | 0.05 | 0.05 | 0.0080 | 34.9 |
| 20 | L (−) Cystine | 0.05 | 0.1 | 0.05 | 0.0080 | 2.4 |
| 21 | DL-Serine | 0.05 | 0.05 | 0.05 | 0.0080 | 51.9 |
| 22 | L (+) Cystine | 0.05 | 0.05 | 0.05 | 0.008 | completely decomposed in less than 1 min. |
| 23 | L-Valine | 0.05 | 0.05 | 0.05 | 0.008 | 75.2 |
| 24 | 4-hydroxyproline | 0.05 | 0.05 | 0.05 | 0.008 | 3.0 |
| 25 | DL-Methionine | 0.05 | 0.0501 | 0.05 | 0.008 | 1.3 |
| 26 | L (−) Proline | 0.05 | 0.05 | 0.05 | 0.008 | 1.8 |
| 27 | DL - Alanine | 0.05 | 0.05 | 0.05 | 0.008 | 54.2 |
| 28 | L (+) Arginine | 0.05 | 0.0657 | 0.05 | 0.008 | 48.0 |
| 29 | L - Histidine | 0.05 | 0.0528 | 0.05 | 0.008 | 39.8 |
| 30 | L - Isoleucine | 0.05 | 0.0509 | 0.05 | 0.008 | 76.5 |
| 31 | DL - Phenylalanine | 0.05 | 0.054 | 0.05 | 0.008 | 37.9 |
| 32 | L - Asparagine | 0.05 | 0.0535 | 0.05 | 0.008 | 13.8 |

-continued

| Exp. | Nitrogen Compound, | Amt. | NaOH Amt. | NaCl Amt. | NaOCl Amt. | 50% Decomposed |
|---|---|---|---|---|---|---|
| 33 | L (+) Glutamine | 0.05 | 0.0537 | 0.05 | 0.008 | 28.0 |
| 34 | DL Ornithine hydrochloride | 0.05 | 0.089 | 0.011 | 0.008 | 38.9 |
| 35 | Aniline - 2 - sulfonic acid | 0.05 | 0.05 | 0.05 | 0.008 | 5.0 |
| 36 | Sulfanilic acid | 0.05 | 0.05 | 0.05 | 0.008 | 1.1 |
| 37 | Metanilic acid | 0.05 | none | 0.05 | 0.008 | 1.25 |
| 38* | Glycine | 0.05 | 0.05 | 0.05 | 0.0079 | 91.4 |
| 39* | Glycine | 0.05 | 0.025 | 0.025 | 0.0038 | 36.2 |
| 40 | N-octadecanylglycine | 0.05 | 0.05 | 0.05 | 0.008 | ** |
| 41 | Aminomethanesulfonic acid | 0.05 | 0.05 | 0.05 | 0.008 | |
| 42 | N-glycylclycine | 0.05 | 0.05 | 0.05 | 0.008 | *** |
| 43 | N,N¹-glyclyglycylglycine | 0.05 | 0.05 | 0.05 | 0.008 | Less than 3 Min. |

*In Experiment 38 in place of the sodium compounds there were used the corresponding lithium compounds (LiOH, LiCl and LiOCl) and in Experiment 39 in place of the sodium compounds there were used the corresponding calcium compounds ($Ca(OH)_2$, $CaCl_2$ and $Ca(OCl)_2$).
**Titration impossible - emulsion developed
***Titration impossible - color developed

EXAMPLE 7

| Toothpaste Formulation | |
|---|---|
| Glycerine | 47 parts |
| Water | 7.3 |
| Saccharin (sodium salt) | 0.04 |
| Precipitated chalk | 20.8 |
| Magnesium Carbonate | 13.3 |
| Magnesium hydroxide | 4.2 |
| Soap (powdered, neutral, white) | 0.85 |
| Gum tragacanth powder | 0.76 |
| N-chlorosarcosine | 5 |
| Toothpowder Formulation | |
| Sodium chloride | 44 parts |
| Sodium bicarbonate | 24 |
| Calcium carbonate | 21.5 |
| Tricalcium phosphate | 5 |
| Potassium chloride | 3.5 |
| Magnesium sulfate | 1.75 |
| N-chlorosulfamic acid | 5 |

What is claimed is:

1. An aqueous composition consisting essentially of water, an N-haloamino-alkanoic acid having 2 to 11 carbon atoms, said halogen having an atomic weight of 35 to 127 and a sufficient amount of an alkali metal phosphate or borate buffer to maintain the pH at 8 to 12.

2. A composition according to claim 1 wherein the N-halo compound is N-halo N-acetyl glycine.

3. A composition according to claim 1 wherein the N-halo compound is N-halo ethylenediamine tetraacetic acid.

4. A composition according to claim 1 wherein the buffer is disodium hydrogen phosphate.

5. A composition according to claim 1 wherein the buffer is $Na_2B_4O_7$.

6. A composition according to claim 1 wherein the pH is 10.5 to 11.5.

7. A composition according to claim 1 wherein the pH is 9.65 to 11.86.

8. A composition according to claim 1 wherein the buffer is a non-toxic phosphate or borate compatible with said N-haloaminoalkanoic acid.

9. A composition according to claim 1 wherein the N-halo compound is N-haloglycine.

10. A composition according to claim 9 wherein the N-haloglycine is N-chloroglycine.

11. A composition according to claim 9 wherein the N-haloglycine is N-bromoglycine or N-iodoglycine.

* * * * *